(12) United States Patent
Valia et al.

(10) Patent No.: US 10,632,060 B2
(45) Date of Patent: Apr. 28, 2020

(54) NAIL COMPOSITION WITH CAPPED OLIGOMERS

(71) Applicant: Revlon Consumer PRoducts Corporation, New York, NY (US)

(72) Inventors: David Valia, San Diego, CA (US); Robert Sandewicz, Monroe Township, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 16/017,007

(22) Filed: Jun. 25, 2018

(65) Prior Publication Data

US 2019/0388332 A1    Dec. 26, 2019

Related U.S. Application Data

(63) Continuation of application No. PCT/US2017/012811, filed on Jan. 10, 2017.

(60) Provisional application No. 62/278,655, filed on Jan. 14, 2016.

(51) Int. Cl.
*A61K 8/87* (2006.01)
*A61K 8/86* (2006.01)
*A61Q 3/02* (2006.01)

(52) U.S. Cl.
CPC .................. *A61K 8/87* (2013.01); *A61K 8/86* (2013.01); *A61Q 3/02* (2013.01); *A61K 2800/81* (2013.01); *A61K 2800/94* (2013.01); *A61K 2800/95* (2013.01)

(58) Field of Classification Search
CPC ... A61Q 3/02; A61K 8/87; A61K 8/86; A61K 2800/80; A61K 2800/81; A61K 2800/94
See application file for complete search history.

(56) References Cited

U.S. PATENT DOCUMENTS

| 6,403,063 | B1 | 6/2002 | Sawyer | |
|---|---|---|---|---|
| 6,433,073 | B1 | 8/2002 | Kantner et al. | |
| 2002/0146382 | A1 | 10/2002 | Mallo et al. | |
| 2006/0052571 | A1 | 3/2006 | Heischkel | |
| 2013/0263875 | A1* | 10/2013 | Burgess | A45D 29/00 132/200 |
| 2015/0359724 | A1* | 12/2015 | Ijdo | A61K 8/87 424/61 |
| 2016/0000675 | A1* | 1/2016 | Hosseinpour | A61K 8/44 132/200 |

FOREIGN PATENT DOCUMENTS

| EP | 1380281 | 1/2004 |
|---|---|---|
| KR | 20150066808 | 6/2015 |
| WO | WO2013-106222 | 7/2013 |
| WO | WO2014-176275 | 10/2014 |

OTHER PUBLICATIONS

EP17738789 search report, (family member application).
PCT/US17/12811 search rep, (parent application).

* cited by examiner

*Primary Examiner* — Yanzhi Zhang
(74) *Attorney, Agent, or Firm* — Dorsey & Whitney LLP

(57) ABSTRACT

The present disclosure relates generally to a composition comprising at least one capped oligomer, at least one solvent, at least one film former, and at least one monomer or polymer, said composition having a sward hardness <10 and >1 when applied to a glass plate.

15 Claims, 1 Drawing Sheet

NAIL COMPOSITION WITH CAPPED OLIGOMERS

FIELD

The present disclosure relates generally to compositions for nail coatings, and particularly, but not by way of limitation, to compositions containing capped oligomers that provide improved adhesion, durability/toughness, and scratch resistance, as well as improved solvent removability.

This application claims priority from co-pending application Serial Number PCT/US2017/012811 filed Jan. 10, 2017 claiming priority to now expired provisional application U.S. 62/278,655 filed Jan. 14, 2016, the entire disclosures of which are hereby incorporated by reference.

BACKGROUND

The information provided below is not admitted to be prior art to the present invention, but is provided solely to assist the understanding of the reader.

Photo-reactive nail coatings provide a durable scratch resistant nail coating with improved adhesion. These photo-reactive coatings contain one or more polymerizable oligomers plus a photo-initiator which upon exposure to UV light of a specific wavelength, cross-link to form the durable, continuous coating on the surfaces of the nail.

The oligomers commonly used in the photo-reactive coatings are urethane dimethacrylate oligomers containing unsaturated sites. The unsaturated sites are capable of undergoing cross-linking when exposed to a UV-light source in the presence of a suitable photo-initiator. These oligomers can be described as polymerizable or "uncapped" oligomers. Compositions containing uncapped oligomers require careful formulation and stabilization to prevent undesirable side reactions or pre-polymerization.

There is a need to develop a durable scratch resistant coating without the undesirable side-reactivity or the need for a UV-light induced cross-linking. The capped oligomers in this disclosure offer a controlled mechanism for providing a durable scratch resistant nail coating.

SUMMARY

In an embodiment of this disclosure comprises a composition composed of at least one capped oligomer, at least one solvent, at least one film former and said composition having a 2 hour sward hardness <10 and >1 when applied to a glass plate.

In another embodiment of this disclosure the composition comprises at least two layers of compositions having different functions on the nail, each layer contains at least one capped oligomer, at least one solvent, at least one film former and each composition has a 2 hour sward hardness <10 and >1 when applied to a glass plate. The layers can be a basecoat Layer and a color layer or a color layer and a topcoat layer.

The compositions disclosed herein can be applied to natural or synthetic nails. A nail is a horny sheath or synthetic sheath protecting the upper end of each finger and toe of humans and most other primates.

In an embodiment the capped oligomer disclosed herein is a urethane oligomer. Non-limiting examples of capped urethane oligomers are Bis-Ethylhexanol Poly (1,4-Butanediol)-13/IPDI Copolymer and Bis-Ethylhexanol Poly (Caprolactone Neopentyl Glycol)/IPDI Copolymer.

In an embodiment the composition disclosed herein can include at least one photoinitiator. Examples of photoinitiators include, but are not limited to, benzoylphenylphosphinates, cyclohexylphenyl ketones, benzyl ketals, 2,4,6-trimethylbenzoyldiphenylphosphinate, hydroxycyclohexyl phenyl ketone, benzyl dimethyl ketal, and mixtures thereof.

In an embodiment of the composition disclosed herein the composition contains a polymer. An example of a polymer in the composition is an ester.

In an embodiment of the composition disclosed herein the composition contains a monomer. A monomer is a compound whose molecules can join together to form a polymer. A non-limiting example of a monomer in the composition is an oil.

In an embodiment of the composition disclosed herein the composition contains a solvent which can include, but is not limited to, a ketone, and alkyl acetate, an alcohol, an alkane, an alkene, acetone, ethyl acetate, butyl acetate, isopropyl alcohol, ethanol, methyl ethyl ketone, toluene, hexane, and mixtures thereof.

In an embodiment the composition disclosed herein contains an adhesion-promoting (meth)acrylate. Examples of adhesion-promoting (meth)acrylate include, but are not limited to, tetrahydrofurfural methacrylate, ethyl methacrylate, pyromellitic dianhydride glyceryl dimethacrylate, and mixtures thereof.

In an embodiment the composition disclosed herein may contain at least one plasticizer.

In an embodiment the composition further contains at least one coloring agent. Examples of coloring agents include, but are not limited to, pigments and dyes which can be dispersed in the solvent and stay suspended in the composition over time.

BRIEF DESCRIPTION OF THE DRAWINGS

The foregoing and other features and advantages of the invention will be apparent from the following, more particular description of embodiments of the invention, as illustrated in the accompanying drawings wherein:

FIG. 1 is a graph showing the hardness of the various formulations (y axis) vs time in hours (h) and days (d) (X axis) of a commercial production sample of clear nail enamel modified as described in this disclosure. In the graph the following represent the various prepared samples.
  1135-32.4: SYMBOL X
  1135-32.5: SYMBOL GREY;
  1135-32.6: SYMBOL BLACK;
  1135-32.7: SYMBOL 0;
  1135-32.8: SYMBOL©; and
  1135-32.9: SYMBOL,triangle

DESCRIPTION

Embodiments of the present invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. While a number of embodiments and features are described herein, it is to be understood that the various features of the invention and aspects of embodiments, even if described separately, may be combined unless mutually exclusive or contrary to the specific description. All references cited herein are incorporated by reference as if each had been individually incorporated.

The present disclosure relates generally to a composition composed of at least one capped oligomer, at least one solvent, at least one film former, said composition having a 2 hour sward hardness <10 and >1 when applied to a glass plate. The composition can comprise a single thickness (layer) or at least two layers of compositions having different functions on the nail, each layer contains at least one capped oligomer, at least one solvent, at least one film former, and each composition has a 2 hour sward hardness <10 and >1 when applied to a glass plate. The layers can be a basecoat layer and a color layer or a color layer and a topcoat layer.

As used in the present disclosure the compositions may be applied to a natural nail or a synthetic nail. The natural nail is the natural keratinous material known as fingernails and toenails. Synthetic nails are comprised of chemically reactive monomers, and/or oligomers, in combination with reactive or non-reactive polymers to create systems which are typically 100% solids and do not require non-reactive solvents. Upon pre-mixing and subsequent application to the natural nail, or application and exposure to UV radiation, a chemical reaction ensues resulting in the formation of a long lasting, highly durable cross-linked nail coating that is difficult to remove. Artificial nails may possess greatly enhanced adhesion, durability, as well as scratch and solvent resistance when compared to nail polishes. However, because of these inherent properties, such coatings are much harder to remove, should the consumer so desire. Removal typically requires soaking in non-reactive solvents for 30-90 minutes (for acrylics and currently available "soakable gels"; it may take more than 90 minutes if ever to remove traditional UV nail gels by solvent) and typically may also require heavily abrading the surface or scraping with a wooden or metal probe to assist the removal process.

As used herein a solvent is a substance that dissolves another substance.

Nail coatings have traditionally been be classified into two categories: nail polishes; also known as lacquers, varnish or enamels and artificial nails; also known as gels or acrylics. Nail polishes typically comprise various solid components which are dissolved and/or suspended in non-reactive solvents. Upon application and drying, the solids deposit on the nail surface as a clear, translucent or colored film. Typically, nail polishes are easily scratched and are easily removed with solvent, usually within one minute and if not removed as described, will chip or peel from the natural nail in one to five days.

As used herein hardness refers to a flexible composition for coating nails. If the coating is too hard the composition is not flexible and will crack with wear. If the coating is too soft, the composition will easily be wiped or washed off with wear. The desired composition is neither too hard nor too soft.

"Sward hardness" is a test that provides a numerical value for hardness for a dried coating. This test uses a measurement device called a "Sward Hardness Rocker", which consists of 2 cylindrical stainless steel rings and a digital measurement apparatus. This instrument operates on the principle that the amplitude of oscillation of the cylindrical rocker decreases more rapidly as the coating surface on which the test is performed becomes softer. A softer coating tends to reduce the number of oscillations of the rocker, while a harder coating film tends to increase the number of oscillations of the rocker. The digital measurement apparatus counts the number of oscillations completed by the instrument and conveys this information to the operator by means of a digital numerical display screen. A lower numerical Sward Hardness value signifies a softer coating, while a higher numerical Sward Hardness value signifies a harder coating. This method is well known in the coatings industry; it is described more formally in ASTM Test Method D2134.

As used herein the capped oligomer is a urethane oligomer labeled (1) below:

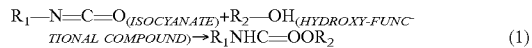

$$R_1\!-\!N\!=\!C\!=\!O_{(ISOCYANATE)}+R_2\!-\!OH_{(HYDROXY\text{-}FUNC\text{-}TIONAL\ COMPOUND)}\!\rightarrow\!R_1NHC\!=\!OOR_2 \quad (1)$$

Non-limiting examples of capped oligomers include Bis-Ethylhexanol Poly (1,4-Butanediol)-13/IPDI copolymer and Bis-Ethylhexanol Poly (Caprolactone Neopentyl 13/IPDI copolymer.

As used herein a capped oligomer is an oligomer combined with one or more compounds to stop further reaction at a reaction site on the oligomer when the oligomer is combined with other compounds.

Certain embodiments of the composition comprise at least one polymer which conveys enhanced adhesiveness and which confers solvent sensitivity to the composition. The presence of certain polymers creating interfacial bonds, renders the bonds susceptible to rupture by organic solvents.

According to an aspect, a polymer which conveys both enhanced adhesion and which sensitizes the polymer interfacial bond to solvent may be an ester. Non-limiting examples include a cellulose ester. According to a particular aspect, the non-reactive, solvent-dissolvable polymer is nitrocellulose and/or optionally a cellulose mixed ester such as a cellulose acetate alkylate. According to a more particular aspect, the non-reactive, solvent-dissolvable polymer is a nitrocellulose and/or cellulose acetate butyrate and/or a cellulose acetate propionate. The non-reactive, solvent-dissolvable polymer may be a mixture of any acceptable polymer. According to a further aspect, the non-reactive, solvent-dissolvable polymer may be present at from about 0 to about 75 weight %.

As used herein a polymer is a chemical compound that is made of small molecules that are arranged in a simple repeating structure to form a larger molecule.

Certain embodiments of the composition comprise at least one monomer which imparts to the interfacial bonds a high degree of sensitivity to organic solvent. According to an aspect, the monomer is an oil. Non-limiting examples include acetyl tributyl citrate, triacetin, propylene glycol monobenzoate, dipropylene glycol dibenzoate, glyceryl triacetate, diethylhexyl malate and similar compounds. According to an aspect, such monomers are present at from about 0 to about 70 weight % of the composition.

As used herein, the expression "at least one" means one or more and thus includes individual components as well as mixtures and combinations.

The cosmetic compositions and methods of the present disclosure consist of, or consist essentially of the elements and limitations described herein, as well as any additional or optional ingredients, components, or limitations otherwise useful as found in personal care compositions intended for application to nail coatings. A person skilled in the art will take care to select the optional additional additives and/or the amount thereof such that the advantageous properties of the composition according to the invention are not, or are not substantially, adversely affected by the envisaged addition. These substances may be selected variously by the person skilled in the art in order to prepare a composition which has the desired properties, for example, consistency or texture. These additives may be present in the composition in a proportion from 0% to 99% (such as from 0.01% to 90%) relative to the total weight of the composition and further such as from 0.1% to 50% (if present).

According to the present disclosure, the compositions may comprise a color layer. The color layer contains at least one coloring agent (colorant). Suitable coloring agents include but are not limited to pigments, dyes, such as liposoluble dyes, nacreous pigments, and pearling agents.

According to the present disclosure, the compositions may comprise a basecoat or topcoat layer. In the basecoat or topcoat layer the composition is a clear or transparent prior to (basecoat) or after (topcoat) application of the color layer. However, it is possible that topcoats and basecoats could contain colorants.

A basecoat can be described as a layer intermediate between the natural or synthetic nail and coating surfaces. The disclosed basecoat is a polymerizable liquid so as to provide a completely conformal coating over the nail surface.

A topcoat can be described as a protective topcoat layer to be applied to an exposed surface of the color layer.

According to the present disclosure layers of composition describe the application of nail coatings. A composition is painted on the nail to provide a cosmetic coloring or a healing or strengthening of the nail. Application is done by painting a composition on the nail. According to an aspect, the nail coating composition is applied, and at least partially dried as three, distinct layers. According to an aspect, application of any one of the Layers may be omitted. According to an aspect, application of any two of the layers may be omitted. According to an aspect, only a formulation for a color layer comprises colorant agents. According to an aspect, a formulation for any of the layers may comprise colorant.

Representative liposoluble dyes which may be used according to the present invention include Sudan Red, DC Red 17, DC Green 6, .beta.-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, are present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.01% to 40%, and further such as from 2% to 30%. In the case of certain products, the pigments, including nacreous pigments, may, for example, represent up to 50% by weight of the composition.

An embodiment of the composition comprises an adhesion promoting (meth)acrylate. As is known to persons of skill in the polymer arts, the term (meth)acrylate encompasses acrylates and/or methacrylates. According to an aspect, such reactive methacrylates may be selected from the group consisting of hydroxypropyl methacrylate (HPMA), hydroxyethyl methacrylate (HEMA), ethyl methacrylate, tetrahydrofurfural methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof. According to an aspect, the polymerized composition increased adhesiveness is present from about 0 to about 50 weight %.

A non-limiting suitable photoinitiator is hydroxycyclohexyl phenyl ketone, which may be obtained under the trade name Igracure, 184 and which may be present from about 0 to about 20 weight % of the composition.

Other non-limiting suitable photoinitiators are benzoylphenylphosphinates, cyclohexylphenyl ketones, benzyl ketals, 2,4,6-trimethylbenzoyldiphenylphosphinate, hydroxycyclohexyl phenyl ketone, benzyl dimethyl ketal and mixtures thereof and which may be present from about 0 to about 20 weight % of the composition.

The compositions of the invention may contain from about 0.001-5% by weight of a plasticizer. The plasticizer causes the polymerized nail structure to have improved flexibility and reduced brittleness. Plasticizers act to minimize the effects of brittleness of the subsequently formed polymer after exposure to UV radiation, sun light, or air. Plasticizers also are found to slightly shorten the removal time. Plasticizers may be present at from 0 to about 25 weight % of the composition. Persons of skill in the polymer arts will appreciate that inclusion of plasticizers above a certain limit is undesirable because they may impair the integrity and durability of the coatings. Suitable plasticizers may be esters, low volatility solvents, or non-ionic materials such as nonionic organic surfactants or silicones.

In certain embodiments, the removable, adhesion-promoting nail coating composition further comprises to 5 weight % of a plasticizer selected from the group consisting of esters, low volatility solvents (paraffinic hydrocarbons, butyrolactone, xylene, methyl isobutyl ketone), non-ionic surfactants, non-ionic silicones, isostearyl isononanoate, silicones, diisobutyl adipate, trimethyl pentanyl diisobutyrate, acetyl tributyl citrate, and mixtures thereof.

Suitable esters include those having the general structure RCO—OR' where RCO— represents a carboxylic acid radical and where —OR' is an alcohol residue. Preferably R and R' are fatty radicals, having 6 to 30 carbon atoms, and may be saturated or unsaturated. Examples of suitable esters are those set forth on pages 1558 to 1564 of the C.T.F.A. Cosmetic Ingredient Dictionary and Handbook, Seventh Edition, 1997, which is hereby incorporated by reference. In the preferred compositions of the invention, the plasticizer is an ester of the formula RCO—OR' wherein R and R' are each independently a straight or branched chain $C_{6-30}$ alkyl. A suitable plasticizer is isostearyl isononanoate. Other suitable plasticizers are disclosed in U.S. Pat. No. 6,818,207 which is incorporated by reference.

The composition of the present disclosure may comprises at least one solvent. A suitable solvent is readily volatile at room temperature and is a good solvent for the remaining ingredients. Upon application, the solvent readily volatilizes leaving regions of increased porosity throughout the nail coating. These porous regions later facilitate the entry of a remover solvent which may be acetone.

Example of suitable solvents includes, but is not limited to, ketones, alkyl acetates, alcohols, alkanes, alkenes, and mixtures thereof. Suitable solvents may be selected from the group consisting of acetone, ethyl acetate, butyl acetate, isopropyl alcohol, ethanol, methyl ethyl ketone, toluene, hexane, and mixtures thereof. Typically a solvent or a mixture of solvents is included at up to about 70 weight percent.

In the composition of the present disclosure the term "film former" means a material which, upon drying, produces a continuous film on keratinous substrates such as skin, hair, or nails. The term "film forming polymer" means that the film former is in the polymeric form. A variety of polymers have film forming properties: they can be natural polymers, synthetic polymers, or polymers that have both natural and synthetic portions. When forming a film on nails, it is important that the film have certain properties in order to provide a commercially acceptable product. For example, if the film formed is too brittle, it may crack, or chip from the keratinous surface. On the other hand, if the film is not hard enough, it may be tacky to the touch and the consumer will have the feeling that the product has not dried on the skin. A wide variety of film forming polymers may be used in the cosmetic or personal care products of the invention. The film forming polymer must be capable of forming a film on the skin, nails, or hair. The film forming polymers may be natural or synthetic, or a combination of both, and may be in the form of solids, semi-solids, or liquids. The film forming polymer may be neutral or ionic in character, e.g. anionic, cationic, nonionic, or amphoteric.

Suitable synthetic polymers include homopolymers, copolymers, and block and graft copolymers comprised of repeating monomers such as acrylic or methacrylic acid or esters thereof, urethanes, esters, amides, styrene, vinyl, silicon, and so on. The synthetic polymers may be present in the composition in ranges from 0.1-95%, preferably 1-85%, more preferably 3-45% by weight of the total composition.

Examples of synthetic film forming polymers include, but are not limited to, those set forth in the CTFA Cosmetic Ingredient Dictionary and Handbook, Eighth Edition, 2000, pages 1744 through 1747, which are hereby incorporated by reference, including those which are summarized herein.

EXAMPLE

Table 1 compares combinations of uncapped and capped oligomers with and without photo-initiators. Each experimental sample was evaluated as follows:

A 6-mil test film of each sample was deposited onto a 4"×4" glass plate pre-cleaned with acetone;

Each test film was irradiated (cured) for 2 minutes in a commercially available UV Lamp.

The cured test film was wiped lightly 2 hours post-cure using a facial tissue saturated with isopropyl alcohol; and A Sward Digital Hardness Rocker (Model GS-1, Paul N. Gardner Co., Inc., N.E. 1$^{st}$ Street, Pompano Beach Fla. 33060) was used to measure hardness of the cured films at 2 hrs., 24 hours, and once daily for 7 days post-curing. Sward hardness is measured by placing the Sward Hardness Rocker onto the dried test film, energizing the digital measurement apparatus, gently rotating the rocker by hand about 25-30 degrees from vertical, then gently releasing the rocker until its motion has stopped completely; the Sward Hardness value for the sample is obtained by reading the numerical value shown on the digital readout and multiplying said value by 2.0.

Test samples were prepared in the following manner. Glass tiles, approximately 4"×4"×0.25", were cleaned with acetone and used as a testing substrate for each test formulation using a Bird Film Applicator (3.5" path width, 0.006" wet film thickness; Paul N. Gardner Co., Inc., N.E. 1st Street, Pompano Beach Fla. 33060) a test film was deposited onto the glass tile. Sample films were then cured for 2 minutes using an ultraviolet nail lamp (Model D8200, Creative Nail Design, 1125 Joshua Way, Vista Calif. 92081). Immediately post-cure, as a precaution, all test films were wiped lightly with a facial tissue saturated with isopropyl alcohol, to remove any oxygen inhibition layer that may form during the UV curing process. Test films were stored at ambient temperature and their Sward hardness-versus-time profiles were measured after 2 hours and once daily for seven (7) consecutive days. Test results are presented in the following data tables:

TABLE 1

CAPPED vs. UNCAPPED OLIGOMER STUDY: FILM HARDNESS vs. TIME

| Time:  | 1135-32.4 | 1135-32.5 | 1135-32.6 | 1135-32.7 | 1135-32.8 | 1135-32.9 |
|--------|-----------|-----------|-----------|-----------|-----------|-----------|
| 2 hrs. | 4         | 1         | 1         | 4         | 2         | 2         |
| 24 hrs.| 10        | 4         | 6         | 8         | 8         | 8         |
| 2 day  | 12        | 6         | 8         | 8         | 10        | 8         |
| 3 day  | 12        | 6         | 8         | 8         | 10        | 8         |
| 4 day  | 12        | 6         | 10        | 10        | 12        | 8         |
| 5 day  | 12        | 6         | 8         | 10        | 10        | 10        |
| 6 day  | 14        | 8         | 10        | 12        | 12        | 10        |
| 7 day  | 14        | 6         | 10        | 10        | 12        | 10        |

1135-32.4: No oligomers or photo-initiator;

1135-32.5: 2 capped urethane oligomers (1.5% each Bis-Ethylhexanol Poly (1,4-Butanediol)-13/IPDI Copolymer Neopentyl Glycol)/IPDI Copolymer (80% NV in Ethyl Acetate) and Bis-Ethylhexanol Poly(Caprolactone Neopentyl Glycol)/IPDI Copolymer (80% NV in Ethyl Acetate)+photo-initiator (1.5% Irgacure 819) (BASF Corporation, 100 Park Avenue Florham Park, N.J. 07932);

1135-32.6: 2 uncapped urethan dimethacrylate oligomers (1.5% each UR-CND-1B and UR-CND-3B)+photo-initiator (1.5% Irgacure 819);

1135-32.7: 2 capped urethane oligomers (1.5% each Bis-Ethylhexanol Poly (1,4-Butanediol)-13/IPDI Copolymer (80% NV in Ethyl Acetate) and Bis-Ethylhexanol Poly(Caprolactone Neopentyl Glycol)/IPDI Copolymer (80% NV in Ethyl Acetate); no photo-initiator;

1135-32.8: 2 uncapped urethan dimethacrylate oligomers (1.5% each UR-CND-1B and UR-CND-3B); no photo-initiator; and 1135-32.9: Photo-initiator only (1.5% Irgacure 819); no oligomers.

Addition of either uncapped or capped oligomers clearly produced a reduction in film hardness as compared to control, when used either with or without photo-initiator.

The combination of capped oligomers plus photo-initiator produced the most significant reduction in film hardness as compared to control. Capped oligomers demonstrate the ability to soften nail lacquer films while avoiding potential long-term stability problems that likely would be encountered when using either uncapped oligomers and/or photo-initiator. The addition of either uncapped or capped oligomers clearly produced a reduction in film hardness as compared to control, when used either with or without photo-initiator.

What is claimed is:

1. A composition comprising at least one capped oligomer, at least one solvent, and at least one film former, wherein the capped oligomer is selected from the group of copolymers of isophorone diisocyanate (IPDI) consisting of Bis-Ethylhexanol Poly (1,4-Butanediol)-13/IPDI Copolymer and Bis-Ethylhexanol Poly(Caprolactone Neopentyl Glycol)/IPDI Copolymer and mixtures thereof.

2. The composition of claim 1, wherein the composition is applied to natural or synthetic nails.

3. The composition of claim 1, wherein the capped oligomer is Bis-Ethylhexanol Poly (1,4-Butanediol)-13/IPDI Copolymer.

4. The composition of claim 1, wherein the capped oligomer is Bis-Ethylhexanol Poly(Caprolactone Neopentyl Glycol)/IPDI Copolymer.

5. The composition of claim 1, wherein said composition further comprises at least one photoinitiator.

6. The composition of claim 5, wherein said at least one photoinitiator is selected from the group consisting of benzoylphenylphosphinates, cyclohexylphenyl ketones, benzyl ketals, and mixtures thereof.

7. The composition of claim 5, wherein said at least one photoinitiator is selected from the group consisting of 2,4,6-trimethylbenzoyldiphenylphosphinate, hydroxycyclohexyl phenyl ketone, benzyl dimethyl ketal, and mixtures thereof.

8. The composition of claim 1, wherein the composition further comprises at least one polymer which is an ester.

9. The composition of claim 1, wherein the said composition further comprises at least one monomer or at least one oligomer.

10. The composition of claim 1, wherein the solvent is selected from the group consisting of ketones, alkyl acetates, alcohols, alkanes, alkenes, and mixtures thereof.

11. The composition of claim 1, wherein said solvent is selected from the group consisting of acetone, ethyl acetate, butyl acetate, isopropyl alcohol, ethanol, methyl ethyl ketone, toluene, hexane, and mixtures thereof.

12. The composition of claim 1, wherein the composition further comprises an adhesion-promoting (meth)acrylate.

13. The composition of claim 12, wherein said adhesion-promoting (meth)acrylate is selected from the group consisting of hydroxypropyl methacrylate (HPMA), hydroxyethyl methacrylate (HEMA), ethyl methacrylate, tetrahydrofurfural methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof.

14. The composition of claim 1, further comprising at least one plasticizer.

15. The composition of claim 1, wherein the said composition further comprises at least one oligomer.

* * * * *